US005395392A

United States Patent [19]

Suhonen

[11] Patent Number: 5,395,392

[45] Date of Patent: Mar. 7, 1995

[54] DEVICE FOR THE ORAL ADMINISTRATION OF AN ACTIVE SUBSTANCE FOR PREVENTION OF TOOTH DECAY IN INFANTS

[76] Inventor: Jouko Suhonen, Huswisenstrasse 7, CH-8426 Lufingen, Switzerland

[21] Appl. No.: 200,845

[22] Filed: Feb. 22, 1994

Related U.S. Application Data

[63] Continuation of Ser. No. 844,602, Jun. 1, 1992, abandoned.

[30] Foreign Application Priority Data

Oct. 2, 1989 [CH] Switzerland ........................ 3577/89
Mar. 27, 1990 [DE] Germany ........................ 9003563 U

[51] Int. Cl.[6] ........................ A61J 17/00; A61K 47/48
[52] U.S. Cl. ........................................ 606/234; 604/77
[58] Field of Search .................. 604/77; 606/234–236; 215/11.1

[56] References Cited

U.S. PATENT DOCUMENTS

| | | | |
|---|---|---|---|
| 2,824,561 | 2/1958 | Mueller | 606/234 |
| 3,117,874 | 1/1964 | Horan | 215/11.1 |
| 3,610,248 | 10/1971 | Davidson | 606/236 |
| 3,966,869 | 6/1976 | Kohl | 215/11.1 |
| 4,192,307 | 3/1980 | Baer | 606/236 |

FOREIGN PATENT DOCUMENTS

| | | | |
|---|---|---|---|
| 811133 | 8/1951 | Germany . | |
| 3503777 | 2/1986 | Germany . | |
| 254945 | 1/1945 | Switzerland | 606/234 |
| 357832 | 12/1961 | Switzerland . | |

*Primary Examiner*—Ralph A. Lewis
*Attorney, Agent, or Firm*—Anderson Kill Olick & Oshinsky

[57] ABSTRACT

For the administration of an active substance of tooth decay in infants, a device (10) constructed in the form of a pacifier is provided, whose mouth disk (11) is detachably connected to the mouthpiece (10) whose interior (18) serves as accommodation chamber for the active substance (20), which comprises xylite and/or combinations of xylite and fluorides, such as sodium fluoride, or of xylite with sorbitol and fluorides and which is disposed in the interior (18) in the form of powder or tablets, in which, within the wall section (**13*a*) located within the lower area of the mouthpiece (12), a plurality of perforations (15) are constructed, and in which, in the wall section (13*b*) located within the upper area of the mouthpiece (12), a plurality of preperforated, circular sections (115) are constructed having the smallest dimensions and which can be pressed through so as to form perforations (15) (FIG. 1**).

9 Claims, 3 Drawing Sheets

DEVICE FOR THE ORAL ADMINISTRATION OF AN ACTIVE SUBSTANCE FOR PREVENTION OF TOOTH DECAY IN INFANTS

This is a continuation application of Ser. No. 07/884,602, filed Jun. 1, 1992, now abandoned.

The present invention can be employed in the field of infant care and, more particularly, within the area of preventive measures and relates to a device for the oral administration of an active substance for the prevention of tooth decay in infants. The device include comprising a teat or nipple with a mouth disk or plate and a pacifier-like mouthpiece of rubber or the like provided with perforations, through which, in combination with the saliva of the infant, the active substance is dissolved and dispenses. The mouth disk is detachably connected to the mouthpiece.

In this case, the invention is to a device for the oral administration of an active substance or ingredient over a fairly long period of time as well as to a pacifier for the oral adminstration of an active substance over a prolonged period of time.

BACKGROUND OF THE INVENTION

Dental medicine (prophylactodontia) has for some time been increasingly studying the so-called prevention of dental illnesses such as tooth decay by employing appropriate measures or therapies in juveniles or children.

In several studies that were carried out by different teams of researchers, it was established that xylite is suitable for the prevention of tooth decay.

In addition to its well-documented effect as a non-cariogenic sweetening agent, it was possible to prove for the pentose derivative xylite, as in S. Assev/G. Rolla, "Further studies on the growth inhibition of streptococcus mutans OMZ 175 by xylitol", Acta Path. Microbiol. Immunol. Scand. 94: 102, 1986, also a cariostatic effect. More recent research has produced evidence that xylite possesses an antibacterial, or rather, a bacteriostatic effect as it inhibits the glycolysis of the bacteria. Xylite is probably ingested by bacteria which, however, are not able to utilize this monosaccharide as a source of energy or to convert it into carbohydrate. Xylite is absorbed by the fructose-PTS system and phosphorylated in this process. Xylite phosphate is toxic for the bacteria and has to be dephosporylated and expelled. Xylite prevents the metabolism of streptococcus mutans. The combination of xylite and sorbitol has a synergistic inhibitory effect on the saccharometabolism of streptococcus mutans. With regard to an anti-decay inhibitory effect, xylite is probably the best researched of the monosaccharides. WHO xylitol field studies and chewing gum studies confirm this. Reference is made to the "Collaborative WHO xylitol field studies in Hungary—Three-year caries activity in institutionalized children". Acta. Odont. Scand. 43: 327-347, 1985, as well as to P. Isokangas/J. Tiekso/P. Alanen/K. K, Mäkinen: "Long-term effect of xylitol chewing gum on dental caries", Community dent. Oral. Epidemiol. 17: 200-203, 1989. Further studies are known which confirm the same results.

In more recent studies it was additionally shown how, in the presence of xylite, the level of streptococcus mutans generally decreases, both in dental plaque as well as also in the saliva.

Reference is made here to E. Söderling/K. K. Mäkinen/C.-Y.Chen/H. R. Pape Jr./W. Loesche/P. L. Mäkinen: "Effect of sorbitol, xylitol and xylitol/sorbitol chewing gums on dental plaque", Caries Res. 23: 378-384, 1969.

From this it becomes clear that, in the presence of xylite, the adhesion of the streptococcus mutans bacteria (caries initiator bacteria) to the dental surface is reduced.

Therefore, these studies already clearly show that a prevention of decay in infancy in terms of a primary prevention would be desirable, which, however, is not unproblematical. Since it has been demonstrated that the retention time of xylite in the oral cavity apparently plays an important part, the active substance has to be retained in the mouth for a fairly long period of time with the aid of suitable measures.

In children of an age starting with approximately three or four years, the release of xylite is possible with the aid of chewing gums, candies, lollipops and stick candies, by the agency of which xylite is released only relatively slowly into the oral cavity over a prolonged period of time. But the prevention of decay is already meaningful when commencing from the first deciduous dentition in order to prevent a colonization with streptococcus mutans by means of a primary prevention and achieving hereby a decay-free condition.

But the handing out of chewing gums, candies, etc. is not possible if infants are involved since the same, for the most part, will swallow them at once and the active substance xylite hardly remains, or remains not at all in the oral cavity—no such thing as a prolonged retention time is possible here. To this is added the hazard of an infant asphyxiating.

According to the DE-C-81 11 33, a tranquilizing pacifier for infants is known which is constructed so as to constitute a pacifier which can be filled with a medication and from which the medicine it is filled with mixed with candies of every kind is slowly sucked out through several sucking holes provided in the teat. In this pacifier, the teat is combined with a mouth disk so as to form a sucking portion in such a way that it is possible to detach said teat by pulling so as to render its filling with the medicament possible, in which case it is also possible to attach the teat to the mouthpiece with the aid of of a threaded connection. Perforations in the teat render a removal of the medication possible during the sucking process. The perforations are not directed in such a way as to guide the flow of the medication to quite specific points of the mouth or specifically to the gingiva, for the objective intended to b e achieved with this pacifier consists exclusively in that the medication present in the pacifier interior be drawn out and absorbed by the infant.

That is why it is the object of the invention, while turning away from the reparative dental medicine in occurring cases of decay, to provide, for the primary prevention and causal therapy, a device for infants which makes a post-eruptive optimization of the enamel maturation and the pellicle maturation of the milk teeth possible, as well as providing a colonization inhibition of mutans streptococci on these teeth and with which, in adaptation to the development of the milk teeth, the pathogens leading to decay are effectively combatted in order to avoid a permanent infection.

SUMMARY OF THE INVENTION

With such a device constructed in accordance with the invention, a pacifier for infants is provided which, by virtue of its construction that renders possible an optimal release of the active substance provided in the interior of the mouthpiece, and this in each case in adaptation to the development of the deciduous teeth of the infant. Through the saliva of the infant, small traces of the active substance are dissolved and conveyed into the oral cavity so that infectious agents present in the oral cavity are destroyed. Furthermore, the active substance absorbed by the saliva of the infant is conveyed into the oral cavity, as a result of which the active ingredient contributes to a prophylaxis that prevents the accumulation of the cariogenic microorganisms and bacteria, such as streptococcus mutans, in the oral cavity and their settling there. By these means the oral health is improved. However, with the device containing xylite-NaF, not merely the colonization by streptococcus mutans is combated, but also the post-eruptive—the phase immediately following the deciduous dentition—enamel maturation and the pellicle maturation of the milk teeth is favorably affected and the disposition of these teeth to tooth decay is thus reduced. To this advantage is added the circumstance that the so-called monoclonal antibodies against streptococcus mutans can be administered by means of the device. Monoclonal antibodies play an important role in the prophylaxis of tooth decay. Monoclonal antibodies are in this context administered with the pacifier-like device in the form of a suspension which, by way of example, has a pleasant flavor imparted to it with the aid of xylite-NaF. In addition, it is possible to administer with the device synthetically produced salivary enzymes which possess an antibacterial effect or an inhibitory effect on bacterial growth. The active substance or substances, respectively, are administered in the form of tablets, powder or syrup or in the form of a glutinous, viscous liquid.

In this connection it is of particular advantage that the mouthpiece of the device, within its lower area which, when in use, is facing the lower jaw, is provided with perforations so that the active substance, with the aid of the saliva, is conveyed into the area of the lower growing deciduous teeth since the lower teeth are the first to erupt. With the development of the upper deciduous teeth it will then be necessary that the active substance also reaches this area. It is for this reason that, within the upper area which, when the device is in use, faces the upper jaw, of the mouthpiece of the device, preperforated sections are provided in the mouthpiece wall which, by the application of a slight pressure, can be urged out of the wall surface in order to unblock the perforations so that larger quantities of saliva are supplied to the active substance so as to be able to supply them to the entire oral cavity. The construction of the preperforated sections is such that, due to the sucking motions of the infant, the preperforated sections are not forced out by pressure, this being possible only when a more substantial pressing force is applied, e.g. by the mouthpiece being rolled together or kneaded or the like, the preperforated sections are pressed out of the wall area of the mouthpiece.

A more intensive absorption of the active ingredient by the saliva is achieved by the embodiment described below this embodiment, the mouthpiece is constructed so as to be double-walled. The active substance is then disposed within the interspace between the two walls. Saliva is conveyed into said interspace through the perforations in the outer wall where the saliva absorbs the active substance and subsequently conveys the active substance into the oral cavity. This construction results in the advantage that it is not necessary for the saliva to be brought into the interior of the mouthpiece first, but that, already through minor sucking movements, saliva reaches the active substance without having to cover a long distance and the same is conveyed directly into the oral cavity.

In order to ensure that the perforations within the lower area of the mouthpiece come to be located within the area of the lower deciduous teeth when the pacifier is inserted, the mouth disk is anatomically configured in such a way that a twisting of the pacifier is not possible during the sucking motions. The mouth disk is provided with a mark so as to enable the mother to insert the pacifier correctly into the infant's mouth.

It is proposed, moreover, that the accommodating member be an integral part of that portion on the sucking side in that the latter comprises an internally located, hollow accommodation chamber for holding the active substance provided with perforations or apertures for releasing the active substance from the chamber into the oral cavity.

By preference, the perforations are selected in such a way that the active substance can be released only slowly, i.e. over a prolonged period of time, from the chamber into the oral cavity. It is-also possible for the release of the active substance to take place in such a way that, on the one hand, saliva from the oral cavity penetrates through the perforations into the internally located accommodation space and absorbs active substance there so as to reach the oral cavity once more from the chamber via the perforations.

It is further proposed that the portion on the sucking side, viz. the mouthpiece, be pluggably or screwably detachably connected to the mouth disk. By means of this construction of the portion on the sucking side, it becomes possible for it to be unscrewed from the mouth disk so that, for example, the internally located, hollow accommodation chamber can be supplied with further active substance.

In order to have e.g., an infant regard the sucking process as a pleasant activity, the mouthpiece is preferably fabricated from a rubber-like or an almost flexible, plastic-like material. In this connection it is important, though, that the selected material is resistant to hot water or resistant to sterilization, respectively.

In order to be able to determine whether any active substance remains in the mouthpiece or in the therein located and constructed hollow accommodation chamber, it is further proposed that the mouthpiece be constructed in a transparent fashion.

According to a further embodiment of to the invention it is proposed that the active substance, by way of example, resembling a so-called stick candy or a lollipop, be an integral part of the mouthpiece. In this proposed embodiment variant, at least the mouth piece is provided in the form of a disposable piece which, each time after having been used, is replaced in toto. It is also possible for the entire device to take the form of a disposable device.

The device according to the invention is particularly suitable for the administration of xylite or of xylite/fluoride or xylite (50% by weight) sorbitol/fluoride combinations, but also for the "long-term adminstration" of a medication.

However, in principle, the device is suitable for the oral administration of an active substance over a fairly long period of time for all those persons who are subject to an acute risk of swallowing or asphyxiating when chewing gums, candies, etc. are handed out to them. Apart from infants, such persons may also in particular be older people who no longer are capable of consciously retaining a chewing gum or a tablet that has to be sucked in the mouth over a prolonged period of time.

BRIEF DESCRIPTION OF THE DRAWINGS

Embodiments of the invention are described below with the aid of the drawings. Thus.

DETAILED DESCRIPTION OF THE PREFERRED EMBODIMENT

Figure 1:
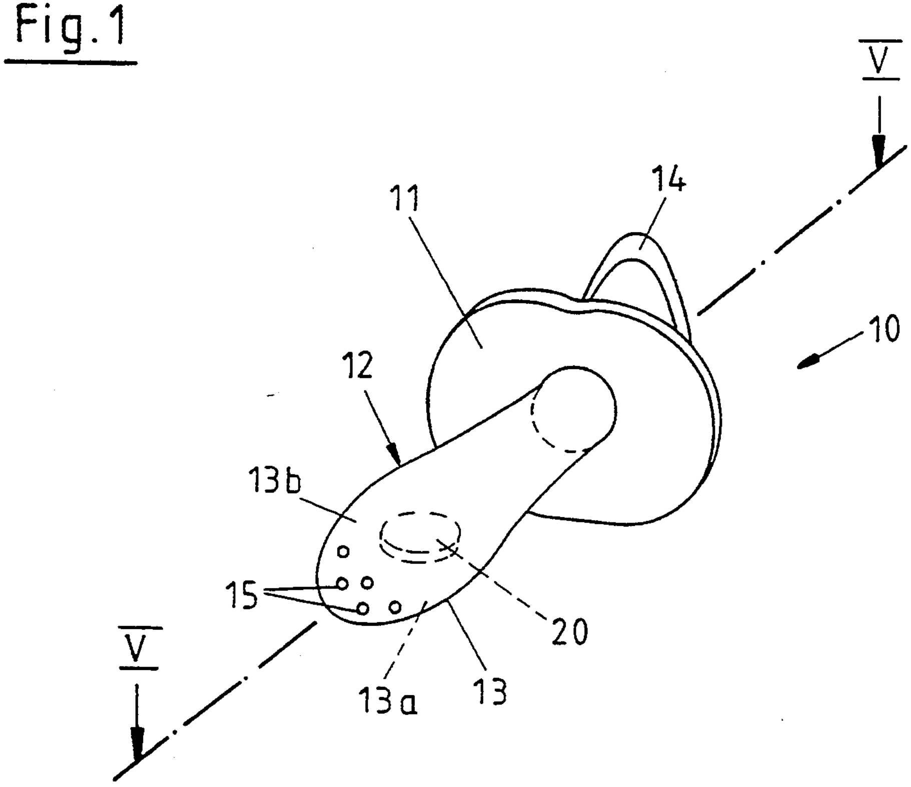
FIG. 1, a diagrammatical view, shows the pacifier-like constructed device for the oral administration of an active substance.

The device illustrated in FIG. 1 and identified with 10 for the oral administration of an active substance is constructed in the form of a pacifier for infants and comprises a mouth disk 11 and a mouthpiece 12 attached rigidly or detachably to the latter, which constitutes the sucking portion of the device 10. The mouth disk 11 constitutes at the same time a mouth guard to prevent swallowing and may be anatomically configured. This mouth guard 11 is fabricated from plastics or other suitable materials. On the side which faces away from the mouthpiece 12, the mouthpiece 12 is provided with a ring 14 so as to make it possible for the device 10 being attached by means of a tape not depicted in the drawing in the proximity of the infant. The mouthpiece 12 of the device 10 is likewise fabricated from rubber or rubber-like plastics; this sucking portion of the device 10 is flexible. It is also possible for crystal-clear or transparent materials to be made use of in the manufacture of the mouthpiece 12. The wall forming the mouthpiece 12 is identified with 13, the interior enclosed by the mouthpiece 12 is identified with 18.

Within the interior 18 of the mouthpiece 12, active substance is disposed in the form of powder, syrup or in tablet form 20. Xylite, monoclonal antibodies or a combination of xylite and fluorides or xylite, fluorides and sorbitol is employed as active substance. As fluorides, sodium fluoride is used in particular. An infection with a bacteria causing tooth decay in infants is prevented with the aid of such an active substance. By means of the saliva carrying the active substance it is ensured that the active substance remains in the oral cavity so that the bacteria which induces the tooth decay can be effectively combated in the oral cavity.

In addition, the mouthpiece 12, in its wall section 13 located within the lower area, is provided with a number of perforations 15 which possess extremely small dimensions for enabling saliva to enter the interior 18 during the sucking process. Due to the circumstance that the mouth disk 11 is anatomically configured in such a way that the device 10, while the same is in the infant's mouth, is unable to twist as a result of the movements of the tongue, the perforations 15, if the device 10 is correctly inserted into the mouth of the infant, always remains within the lower area and are thus facing the milk teeth in the lower jaw, said milk teeth first develop in the lower jaw and, following this, in the upper jaw. It is in this manner that the active substance, with the aid of the saliva, is conveyed first of all directly into the area of the lower deciduous teeth.

Figure 4:
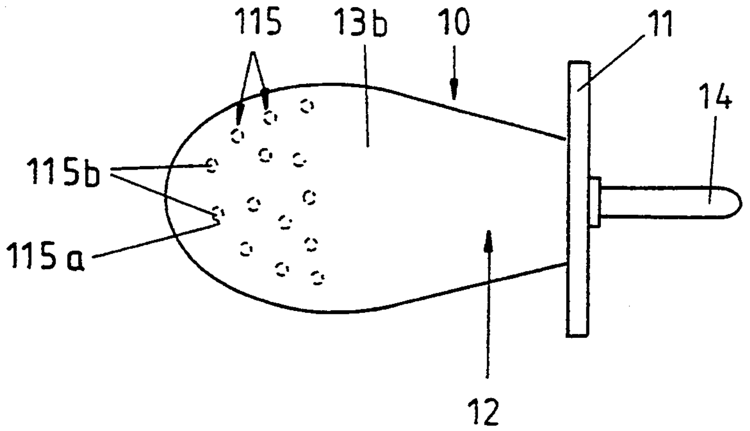
FIG. 4 shows a view from above of the device.

Apart from these perforations 15 within the lower area of the sucking portion of the device 10, the mouthpiece of the same is provided with a further plurality of, at first, closed perforations which are to be found in the wall section **13*b* of the mouthpiece 12 located-within the upper area so as to, following the eruption of the upper deciduous teeth, be able to convey active substance selectively into this upper milk tooth area with the aid of the saliva. Said perforations are formed by preperforated circular sections 115. When these are pressed through, the perforations are unblocked (FIG.4). The preperforated portion is indicated at 115*a*. The sections which can be pressed through are identified with 115*b*. The construction of the preperforated section 115 is such that, due to the sucking motions and the pressure applied by these, the sections 115*b* are not pressed out of the wall area of the mouthpiece 12. It is only by the application of a more substantial pressure that the sections 115*b* are rendered suitable for being pressed out so that then, within the upper wall section 13*b*, the perforations can be formed. In this connection it is possible for the perforations 15 or 115 to extend as far as to the stem-like end 12*a* of the mouthpiece 12**.

Figure 5:
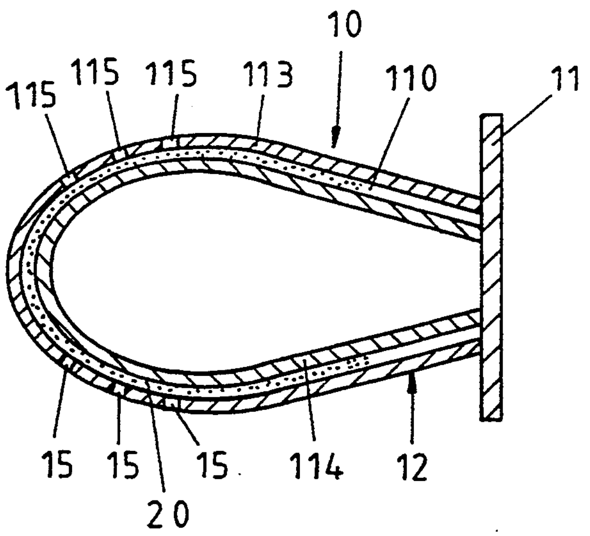
FIG. 5 shows a vertical longitudinal section in the direction of the Line V—V in FIG. 1.

According to a further embodiment according to FIG. 5, the mouthpiece 12 of the device 10 is constructed so as to be double-walled. In the interspace 110 formed between the two walls 113,114, of which the wall 113 forms the outer wall and the wall 114 the inner wall, the active substance 20 is disposed which may e.g. be in the form of a powder or granules. In the outer wall 113, within the lower area of the mouthpiece 12, the perforations 15, and, within the upper area, the sections that can be pressed out **115*b* are disposed or formed; in which connection the possibility exists of providing also within the upper area of the mouthpiece 12, perforations 15** which correspond to those within the lower area.

If the active substance is in the form of powder, in that case the perforations 15 are constructed in such away that saliva is able to penetrate on both sides, but that the powdery active substance 20 is unable to escape through the perforations.

The wall 13 of the mouthpiece 12 is, by preference, fabricated from crystal-clear or transparent materials so that it is possible to make out from the outside whether any active substance still remains in the interior 18 of the mouthpiece 12. In the double-walled embodiment of the mouthpiece 12, the outer wall 113 is fabricated from crystal-clear or transparent materials since, in this case, the active substance is disposed in the interspace 110 between the two walls 113,114. The inner wall 114 is in this case fabricated from opaque materials that are suitable as a material for the mouthpiece 12, flavorless and possess the elasticity of rubber.

Figure 2:
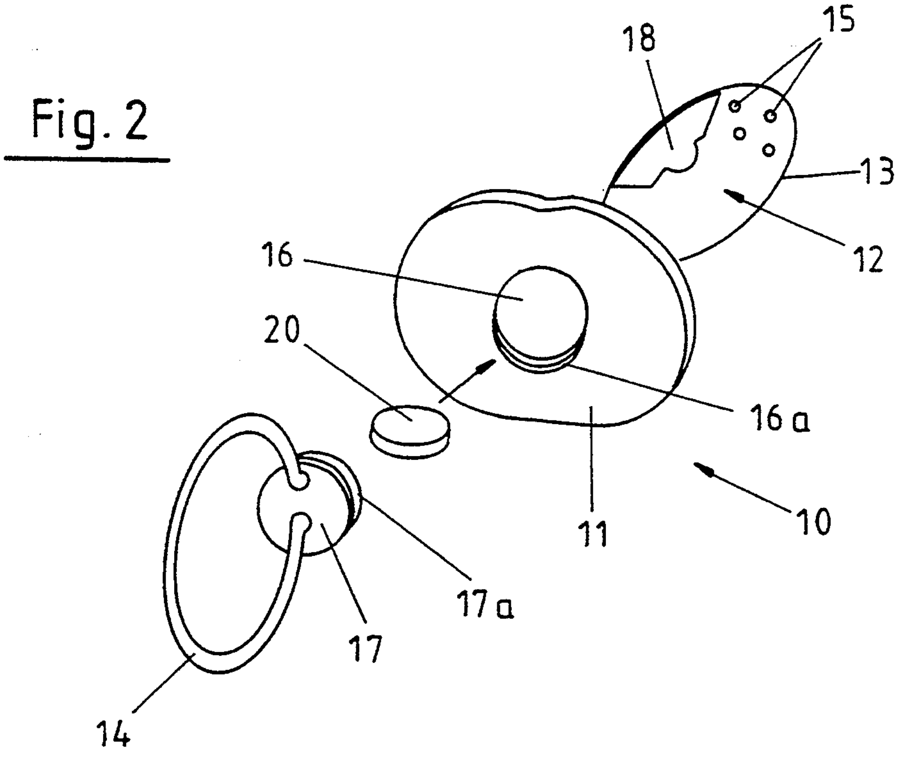
FIG. 2 shows a diagrammatical view of the device according to claim 1.
Figure 3:
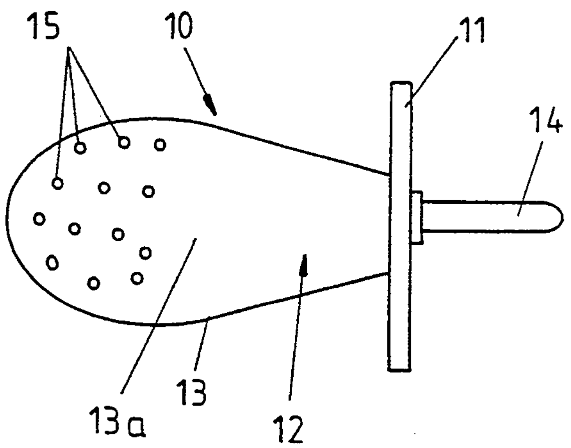
FIG. 3 shows a view from below of the device.

As to the embodiment shown in FIG. 2, the mouth disk 11 of the device 10 has a central perforation 16 with an internal thread 16*a*. This perforation 16 serves for the introduction of the active substance 20 into the interior 18 of the mouthpiece 12 which is attached to the mouth disk 11 within the area of the perforation 16, said mouth disk being dimensioned in such a way that it serves as a safeguard against the mouthpiece being swallowed. The ring 14 is secured to a plate-shaped or disk-shaped screwing portion 17 which is provided with an external thread and dimensioned in such a way that the screwing portion 17 can be screwed into the perforation 16 so as to close the same.

When the active substance 20 is to be introduced in the form of a tablet, powder or syrup containing xylite, a xylite/fluoride or a xylite/sorbitol/fluoride combination, the screwing portion 17 is unscrewed from the perforation 16 so that the interior 18 is now-open on one side. The tablet 20 is introduced and the screwing portion is once more screwed into the perforation 16 so that the interior 18 is closed.

The device 10, that is to say the pacifier, is thusly prepared introduced into the oral cavity of an infant who, as a result of a natural reflex, begins to suck the mouthpiece 12. Owing to the penetration of the saliva through the openings or perforations 15 into the interior 18, the tablet 20 is partially dissolved and active substance is released for absorption into the saliva. By the sucking movements of the infant, the saliva charged with xylite is again drawn through the perforations 15 into the oral cavity, due to this xylite is now released into the oral cavity.

Depending on the shape of the tablet 20, it is possible for such a concentration of xylite to be maintained within the infant's oral cavity over a fairly long period, whereby the streptococcus mutans or the decay-initiating bacteria are effectively combated.

That part of the device 10 which accommodates the active substance 20 in its interior is comprised of material pervious to the active substance, such as rubber or flavorless suitable plastics which do not jeopardize the health.

If perforations are provided in the mouthpiece through which the active substance can be given off to the infant when saliva flows in, other suitable materials may be employed for the fabrication of the mouthpiece.

Moreover, the possibility also exists of constructing the mouthpiece 12 of the device 10 in the form of a shaped member which is comprised solely of the active substance 20. The mouthpiece constructed in this way is then used by the infant sucking the same.

Figure 6:
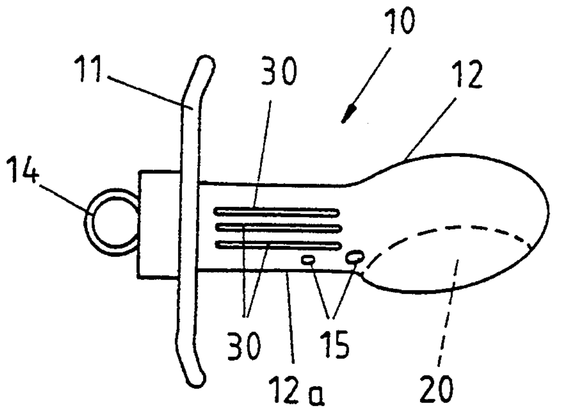
FIG. 6, in a side elevation, shows a further embodiment of the pacifier-like device with reinforcements of the stem-like end of the mouthpiece.

For orthodontic reasons, an anatomical configuration is preferred for the mouthpiece 12 of the device 10, other configurations also appear to be suitable within this context. In order to prevent damage by biting into the stem-like end 12*a* of the mouthpiece 12, the stem-like end 12*a* is, on the outer wall side, provided with a plurality of bead-like reinforcements 30 proceeding in the longitudinal direction of the device, which are comprised of rubber-elastic materials, more particularly of silicon rubber. Said reinforcements 30 may also be formed from material of the mouthpiece 12 (FIG. 6).

Figure 7:
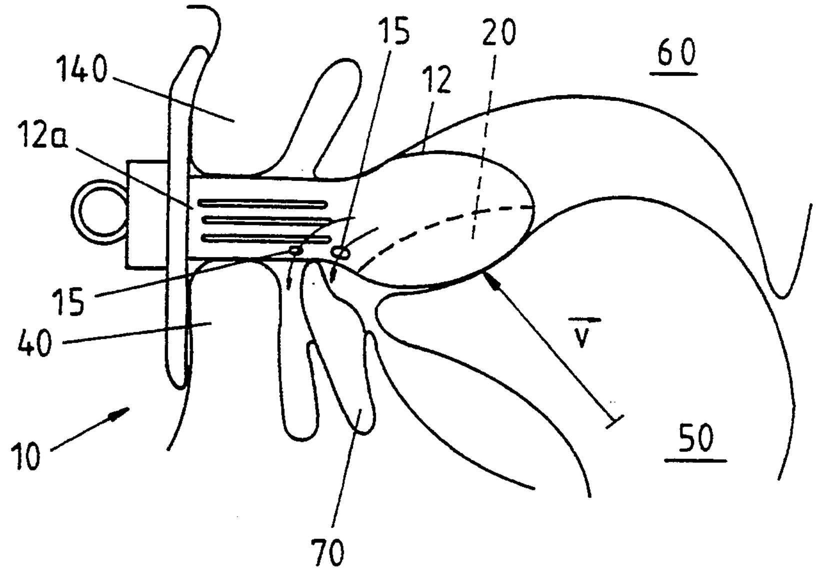
FIG. 7, in a side elevation, shows the mode of function of the device in connection with a lower deciduous tooth.
Figure 8:
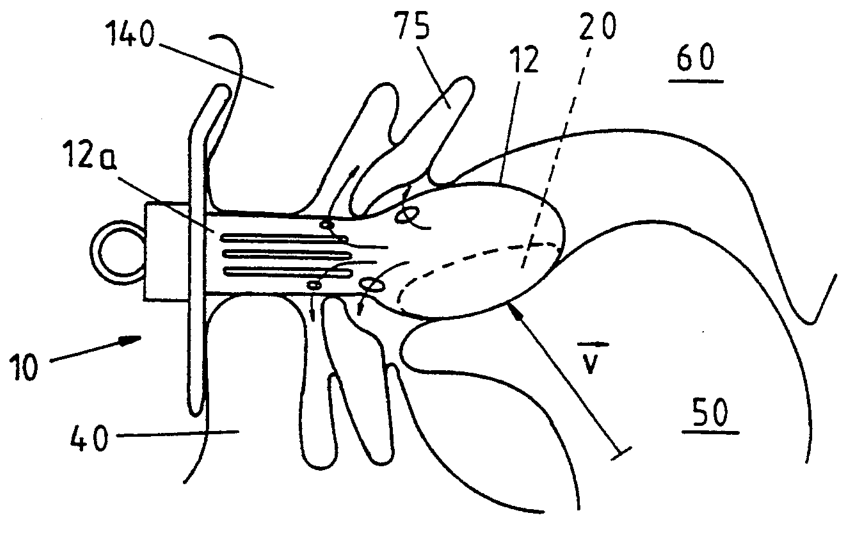
FIG. 8, in a side elevation, shows the mode of function of the device in connection with an upper deciduous tooth.

In the FIGS. 7 and 8, the lower lip is identified with 40 and the upper lip with 140, the tongue with 50, the palate of the oral cavity with 60 and the lower, first milk tooth with 70 and the upper milk tooth with 75.

The lower perforations 15 are provided in the mouthpiece 12 in such a way that the active substance flows, due to the swallowing process and to the lingual pressure, in the direction of the first deciduous teeth 70 (FIG. 7). When further milk teeth erupt, i.e. the upper milk teeth 75, the perforations 115 are adapted to the new situation so that the active substance reaches the newly erupted milk teeth surfaces (FIG. 8).

What is claimed is:

1. Device If or the oral administration of an active substance for the prevention of tooth decay in infants, comprising:

a mouth disk (11) adapted for abutment with lips of an comprising:

a pacifier-like mouthpiece (12) having a base detachably affixed to a Surface of the mouth disk, and lower and upper wall sections (13*a*, 13*b*) extending from the base and defining together an interior (18) of the mouthpiece, the interior serving as an accommodation chamber for receiving the active substance;

the lower wall section (13*a*) having perforations extending into the interior for dissolving and dispensing through the perforations the active substance upon contact with saliva of an infant; and the upper wall section having perforated sections (115*a*) which, upon applying pressure thereto, become open perforations communicating with the interior of the mouthpiece.

2. Device according to claim 1, in combination with the active substance comprising at least one of xylite, monoclonal antibodies against sinustans, a combination of xylite and fluorides, and a combination of xylite, sorbitol and fluorides.

3. Device according to claim 2, wherein the active substance is in a form of one of powder, syrup, and tablets.

4. Device for the oral administration of tooth decay in infants, comprising:

a mouth disk (11) adapted for abutment with lips of an infant;

a pacifier-like mouthpiece (12) having a base detachably affixed to the surface of the mouth disk, and lower and upper wall sections (13*a*, 13*b*) extending from the base and defining together an interior (18) of the mouthpiece, the interior serving as accommodation chamber for receiving the active substance; and the upper wall section having preperforated sections (115*a*) which, upon applying pressure thereto, become open perforations communicating with the interior of the mouthpiece.

5. Device according to claim 4, wherein the lower and upper wall sections comprise an inner wall and an outer wall the distance between the inner walls and outer walls is an interspace which defines the accommodation chamber for receiving the active substance, wherein the preperforated sections are provided in the outer wall of the upper wall sections, and wherein perforations are provided in the outer walls of the lower wall section.

6. Device according to claim 5, wherein at least the outer walls of the lower and upper wall sections are formed of transparent plastic materials.

7. Device according to claim 4, wherein the lower and upper wall sections are formed of transparent plastic material.

8. Device according to claim 4, wherein the lower and upper wall sections define together a stem-like end section, the device further comprising longitudinal reinforcing beads formed on an outer surface of the stem-like end section , the reinforcing beads being formed of a rubber elastic material.

9. Device according to claim 8, wherein the rubber elastic material is silicon rubber.

* * * * *